United States Patent [19]

Pu

[11] Patent Number: 5,106,997
[45] Date of Patent: Apr. 21, 1992

[54] SQUARYLIUM DERIVATIVES AND PREPARATION THEREOF

[75] Inventor: Lyong S. Pu, Kanagawa, Japan

[73] Assignee: Fuji Xerox Co., Ltd., Tokyo, Japan

[21] Appl. No.: 586,980

[22] Filed: Sep. 24, 1990

[30] Foreign Application Priority Data

Sep. 26, 1989 [JP] Japan ................... 1-248108
Sep. 26, 1989 [JP] Japan ................... 1-248109

[51] Int. Cl.$^5$ ................ C07C 225/20; C07D 207/12; C07D 207/08
[52] U.S. Cl. .................... 548/532; 548/570; 560/43; 560/44; 564/307
[58] Field of Search ............ 564/307; 560/43, 44; 548/532, 570

[56] References Cited

U.S. PATENT DOCUMENTS

| | | | |
|---|---|---|---|
| 4,607,124 | 8/1986 | Kazmaier et al. | 564/307 X |
| 4,626,485 | 12/1986 | Kin | 564/307 X |
| 4,751,327 | 6/1988 | Kazmaier et al. | 564/307 |
| 4,908,289 | 3/1990 | Tanaka et al. | 564/307 X |

FOREIGN PATENT DOCUMENTS 2249952 10/1987 Japan ................... 564/307

OTHER PUBLICATIONS

Noller; Chemistry of Organic Compounds, 3rd ed., (1965), pp. 252-254, W. B. Saunders Co.-Philadelphia.
Harrison et al., Compendium of Organic Synthetic Methods, p. 251 (1971), Wiley-Interscience, N.Y.
Weygand/Hilgetag; Preparative Organic Chemistry, (1972), p. 458, John Wiley & Sons, N.Y.

*Primary Examiner*—Joseph Paul Brust
*Attorney, Agent, or Firm*—Finnegan, Henderson, Farabow, Garrett and Dunner

[57] ABSTRACT

A novel squarylium derivative represented by general formula (I) and a process for preparing the same are described:

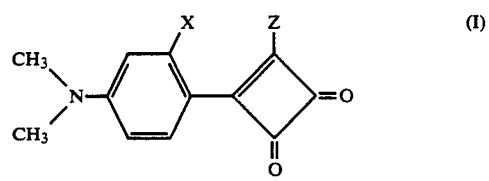

wherein X and Z are defined in the specification. This squarylium derivative exhibits high nonlinearity and is excellent in thermal resistance, light resistance, storage stability and processability, so that it can be used for preparation of nonlinear optical elements.

3 Claims, No Drawings

SQUARYLIUM DERIVATIVES AND PREPARATION THEREOF

FIELD OF THE INVENTION

The present invention relates to a novel squarylium derivative useful as a nonlinear optical material and a process for preparing the same.

BACKGROUND OF THE INVENTION

In the fields of optical communication and optical information processing, nonlinear optical elements play an important role. Nonlinear optical materials used for the nonlinear optical elements are materials which perform very important functions on optical signal processing, such as photomixing generating the sum of frequencies of two kinds of incident light different from each other in frequency, optical parametric producing two kinds of light different from each other in frequency, the Pockels effect and the Kerr effect changing the refractive index of optical media, and secondary harmonic generation (SHG) or tertiary harmonic generation (THG) (i.e., conversion of incident light to a secondary or tertiary harmonic light). As such nonlinear optical materials, inorganic and organic materials have hitherto been discovered.

As the inorganic nonlinear optical materials, the crystals of inorganic compounds such as KDP ($KH_2PO_4$) and lithium niobate ($LiNbO_3$) have been known. However, they were not enough to satisfy fully the requirements.

On the other hand, the organic nonlinear optical materials have recently been noted as materials for new optical elements in the field of optoelectronics, and increasingly investigated year by year. In particular, many investigations for search of materials have been made of organic compounds having $\pi$ electron conjugated systems, because of the high performance and high speed responsibility of their molecular substances.

In general, it has been known that the crystals of the organic nonlinear optical materials are about 10 to 100 times larger in the coefficient of SHG, about 1,000 times higher in optical response speed and also greater in threshold to optical damage than the crystals of the inorganic nonlinear optical materials.

The organic nonlinear optical materials previously known include 2-methyl-4-nitroaniline, m-nitroaniline, N-(4-nitrophenyl)-L-prolinol, 2-acetylamino-4-nitro-N,N-dimethylaniline, 4-dimethylamino-4'-nitro-stilbene, 4'-dimethylamino-N-methyl-4-stilbazolium methyl sulfate and 4'- methylbenzylidene-4-nitroaniline. The nonlinearity of these organic compounds having the $\pi$ electron conjugated systems is caused by the interaction of laser beams as electromagnetic waves with $\pi$ electrons of the organic compounds, and this interaction can be further increased by introducing electron attractive substituents and electron donative substituents into the $\pi$ electron conjugated systems.

In such organic compounds, dipole moments are generally increased, and dipole-dipole interactions in crystallizing become strong, so that central symmetric crystals having a structure in which dipoles of two molecules counteract each other are liable to be formed. There is the problem that the secondary nonlinear optical effect which is important in their applications is not expressed in such central symmetric crystals. In order to put central symmetry into disorder which poses a problem on expression of the nonlinearity in the crystal state, it has been proposed that substituents having hydrogen bonding ability or optically active substituents having asymmetric carbon atoms are introduced into the organic compounds of the $\pi$ electron conjugated systems.

Characteristics generally required for the materials for nonlinear optical elements include the degree of nonlinearity, light permeability, anti-laser damage strength, crystallinity, phase matching property, processability, mechanical strength and hygroscopic property.

It has been very difficult to select a material satisfying the practically required characteristics as described above from the materials for the organic nonlinear optical elements which has hitherto been known.

SUMMARY OF THE INVENTION

An object of the present invention is to provide a practical organic nonlinear optical material having high nonlinear optical effect and improved storage stability and processability.

The present inventors discovered that, even if compounds had large molecular dipole moments and were liable to form the central symmetry in crystallizing, organic nonlinear optical materials particularly high in the secondary nonlinear optical effect were obtained by introducing appropriate substituents into the molecules, and completed this invention.

The above object of the present invention can be attained by a novel squarylium derivative represented by the following general formula (I):

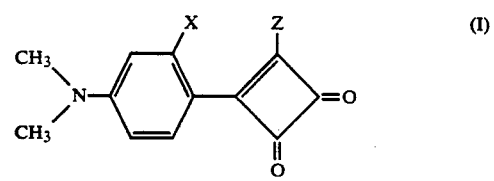

wherein X represents a hydrogen atom, a methyl group, an ethyl group or a methoxy group; and Z represents

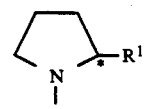

or $-NHR^2$ wherein $R^1$ represents $-CO_2-t-C_4H_9$ or $-CH_2OH$ and $R^2$ represents $-CH_2CH_2OH$,

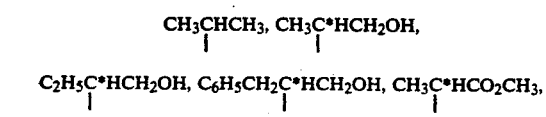

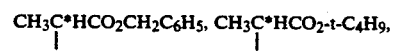

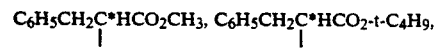

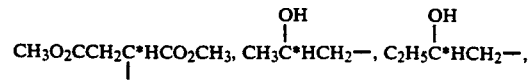

$$\underset{CH_3}{\overset{CH_3}{\diagdown}}CHC^*HCO_2CH_3, \quad \underset{CH_3}{\overset{CH_3}{\diagdown}}CHCH_2C^*HCO_2CH_3,$$

$$\underset{CH_3}{\overset{C_2H_5}{\diagdown}}CHC^*HCO_2CH_3, \quad \underset{CH_3}{\overset{CH_3}{\diagdown}}CHCH_2C^*HCO_2\text{-t-}C_4H_9 \text{ or}$$

$$CH_3\overset{OH}{\underset{|}{C}}HC^*HCO_2CH_3,$$

wherein C* means an asymmetric carbon atom.

DETAILED DESCRIPTION OF THE INVENTION

A cyclobutenedione ring contained in the squarylium derivative of the present invention indicated by the above general formula (I) has a long $\pi$ electron conjugated system as well as electron attraction which is strong similarly with a nitro group, as known from the maximum absorption wavelengths indicated in the examples described later. For that reason, the whole molecule is liable to have a structure in which it is electronically greatly polarized, which contributes to expression of the high nonlinearity. When the substituent having the asymmetric carbon atom is introduced into the squarylium derivative represented by the above general formula (I), the high optical nonlinearity is expressed by controlling molecular orientation in a bulk structure to put the central symmetry into disorder, even if the dipole moment of the molecule itself is large.

The squarylium derivative of the present invention represented by the above general formula (I) can be easily synthesized in high yield according to the following reaction formula:

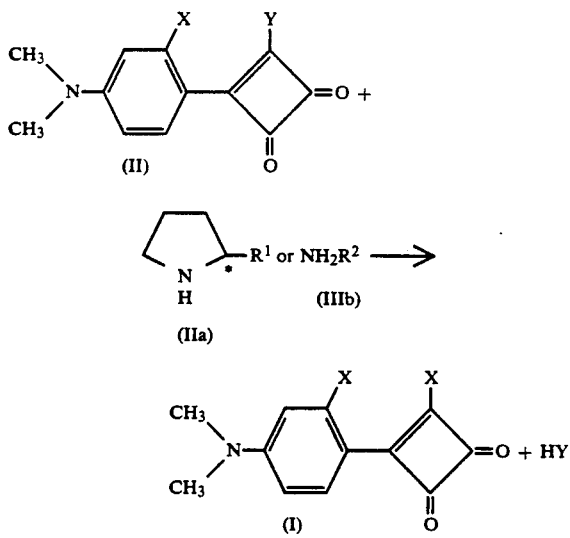

wherein Y represents a chlorine atom, a bromine atom, a methoxy group or an ethoxy group; and Z, $R^1$, $R^2$ and * each have the same meanings as defined above.

Namely, a squarylium derivative represented by general formula (II) is suspended or dissolved in a solvent such as acetone, tetrahydrofuran, methanol or ethanol, and then, an equivalent amount to the above squarylium derivative or more of pyrrolidine compound represented by general formula (IIIa) or an amino compound represented by general formula (IIIb) is added slowly with stirring to the resulting suspension or solution to react them with each other. Usually, the reaction rapidly proceeds, but can be conducted under heating as required. When a product is precipitated with progress of the reaction, it is filtered. When a product is not precipitated, it can be precipitated by concentration of the reaction solution or by addition of an appropriate poor solvent such as n-hexane or methamol. The resulting crystals are purified by recrystallization from a solvent such as an alcohol or acetone or by sublimation.

Instead of the compound represented by the above general formula (IIIa) or (IIIb), an acid addition salt thereof such as a hydrochloride, a bromate or a p-toluenesulfonate can also be used as a raw material to react with the squarylium derivative represented by general formula (II) in the presence of a basic compound such as triethylamine or N-methylmorpholine similarly to the above-described methods. The basic compound is generally added in the reaction system in at least an equivalent amount to the squarylium derivative.

The squarylium derivative represented by the above general formula (II) can be produced in a conventional manner as described in U.S. Pat. No. 4,751,327. For example, a chlorocyclobutenedione derivative is obtained by mixing and stirring a dimethylaniline compound and dichlorocyclobutenedione in a Friedel-Crafts solvent (such as carbon disulfide, nitrobenzene or methylene chloride) in the presence (up to an equivalent amount to the squarylium derivative) of aluminum chloride, and an alkoxycyclobutenedione derivative is obtained by reacting dialkoxycyclobutenedione with a dimethylaniline compound together with a trialkyloxonium salt and a halogenating solvent such as dichloromethane.

The pyrrolidine compounds of general formula (IIIa) and the amino compounds of general formula (IIIb) are commercially available from Aldrich Chemical Co., Ltd., Sigma Chemical Co., or Eastman-Kodak Co.

The present invention is further described by referring to the following Examples and Application Examples.

EXAMPLE 1

Synthesis of 4-(4'-Dimethylaminophenyl)-3-(2'-t-Butoxycarbonyl-pyrrolidinyl)-Cyclobutene-1,2-Dione To 50 ml of an acetone solution of 1 g (4.2 mmol) of a compound represented by the following structural formula (II-1),

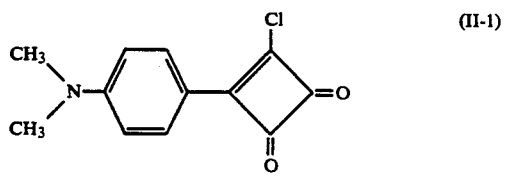

1.5 ml of L-proline-t-butyl ester was added with stirring. After reaction for 2 hours, the solvent was removed by distillation and the residue was recrystallized from methanol to obtain 1.3 g (3.5 mmol) of 4-(4'-dimethylaminophenyl)-3-(2'-t-butoxycarbonylpyrrolidinyl)-cyclobutene-1,2-dione represented by the following structural formula (I') as yellow crystals. The yield was 83%.

pounds described in the column of "general formula (IIIa)" of Table 1 were used as raw materials.

For the resulting products, the elementary analysis values, the maximum absorption wavelengths $\lambda_{max}$ and the melting points were measured. The results thereof are shown in Table 2.

TABLE 1

| Example No. | Formula (II) (Squarylium Derivative) | Formula (IIIa) (Pyrrolidine Compound) | Formula (I) (Objective Product) |
|---|---|---|---|
| 2 | | | |
| 3 | | | |
| 4 | | | |

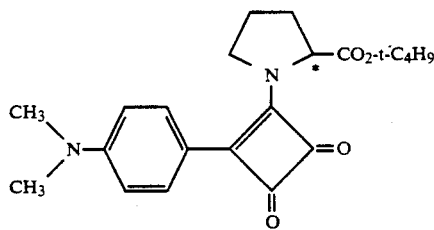

Melting Point: 115° C.
Maximum Absorption Wavelength $\lambda_{max}$: 399 nm (in $CH_2Cl_2$).
Elementary Analysis:

| | Elementary Analysis: | | |
|---|---|---|---|
| | C | H | N |
| Calcd. | 68.08 | 7.08 | 7.56 |
| Found | 67.63 | 7.53 | 7.50 |

EXAMPLES 2 to 5

Objective products described in the column of "general formula (I)" of Table 1 were synthesized in the same manner as in Example 1 with the exception that squarylium derivatives described in the column of "general formula (II)" of Table 1 and pyrrolidine com-

TABLE 2

| Example No. | Elementary Analysis (Calcd./Found) | | | $\lambda_{max}$ (nm) | Melting Point (°C.) |
|---|---|---|---|---|---|
| | C | H | N | | |
| 2 | 69.32/69.45 | 7.59/7.64 | 7.03/7.12 | 393 | 114 |
| 3 | 65.43/65.12 | 6.71/6.68 | 8.48/8.52 | 400 | 53 |
| 4 | 65.98/65.58 | 7.05/7.21 | 7.00/7.10 | 397 | 170 |

EXAMPLE 5

Synthesis of 4-(4'-Dimethylaminophenyl)-3-(2'-Hydroxy-propylamino)-Cyclobutene-1,2-Dione To 100 ml of an acetone solution of 2 g (8.4 mmol) of the compound represented by the above structural formula (II-1) was added 2 g of S-(+)-1-amino-2-propanol, and the heating and stirring were continued for about 2 hours. Yellow crystals were precipitated in the reaction solution. After allowing the reaction solution to stand, the yellow crystals were collected to obtain 2.1 g (7.7 mmol) of 4-(4'-dimethylaminophenyl)-3-(2'-hydroxy-propylamino)-cyclobutene-1,2-dione represented by the following structural formula (I-1) as yellow crystals. The yield was 92%.

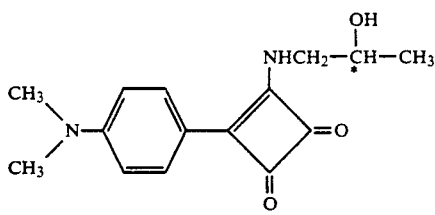

(I-1)

Melting Point: 245° C.

Maximum Absorption Wavelength $\lambda_{max}$: 400 nm (in $CH_2Cl_2$).

Elementary Analysis:

| | Elementary Analysis: | | |
|---|---|---|---|
| | C | H | N |
| Calcd. | 65.67 | 6.61 | 10.21 |
| Found | 65.56 | 6.72 | 10.16 |

EXAMPLE 6

Synthesis of 4-(4'-Dimethylaminophenyl)-3-(2'-Hydroxyethylamino)-Cyclobutene-1,2-Dione To 0.5 g (2.0 mmol) of a compound represented by the following structural formula (II-2) was added 21 ml of ethanolamine, and the mixture was stirred with heating for about 2 hours.

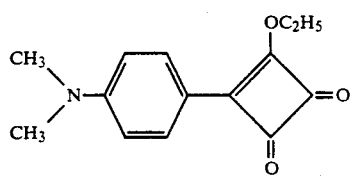

(II-2)

After completion of the reaction, the reaction solution was poured into about 60 ml of water to precipitate the reaction product as yellow crystals. The yellow crystals were collected to obtain 0.32 g (1.2 mmol) of 4-(4'-dimethylaminophenyl)-3-( 2'-hydroxyethylamino)-cyclobutene-1,2-dione represented by the following structural formula (I-2) as yellow crystals. The yield was 60%.

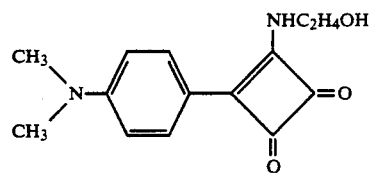

(I-2)

Melting Point: 240° C.

Maximum Absorption Wavelength $\lambda_{max}$: 401 nm (in $CHCl_3$).

Elementary Analysis:

| | Elementary Analysis: | | |
|---|---|---|---|
| | C | H | N |
| Calcd. | 64.61 | 6.20 | 10.76 |
| Found | 64.58 | 6.12 | 10.58 |

EXAMPLE 7

Synthesis of 4-(4'-Dimethylaminophenyl)-3-(1'-Methoxycarbonylethylamino)-Cyclobutene-1,2-Dione To 20 ml of acetone solution containing 0.7 g (5 mmol) of L-alanine methyl ester hydrochloride and 0.6 g (5.6 mmol) of triethylamine was added slowly 20 ml of an acetone solution of 1.0 g (4.2 mmol) of the compound represented by the above structural formula (II-1) to react them one another. After reaction for about 2 hours, water was added thereto to precipitate yellow microcrystals. The precipitated yellow microcrystals were collected to obtain 0.66 g (2.2 mmol) of 4-(4'-dimethylaminophenyl)-3-(1'-methoxycarbonylethylamino)-cyclobutene-1,2-dione represented by the following structural formula (I-3). The yield was 52%.

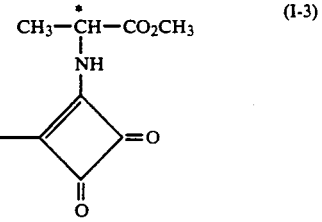

(I-3)

Melting Point: 217° C.

Maximum Absorption Wavelength $\lambda_{max}$: 401 nm (in $CH_2Cl_2$).

Elementary Analysis:

| | Elementary Analysis: | | |
|---|---|---|---|
| | C | H | N |
| Calcd. | 63.56 | 6.00 | 9.27 |
| Found | 63.32 | 5.82 | 9.35 |

EXAMPLES 8 to 37

Objective products described in the column of "general formula (I)" of Table 3 were synthesized in the same manner as with Example 5 with the exception that squarylium derivatives described in the column of "general formula (II)" of Table 3 and amino compounds described in the column of "general formula (IIIb)" of Table 3 were used as raw materials.

For the resulting products, the elementary analysis values, the maximum absorption wavelengths $\lambda_{max}$ and the melting points were measured. The results thereof are shown in Table 4.

TABLE 3

| Example No. | Formula II (Squarylium Derivative) | Formula (IIIb) (Amino Compound) | Formula (I) (Objective Product) |
|---|---|---|---|
| 8 | (CH₃)₂N-C₆H₄-[squarate-Cl] | CH₃*CHCH₂OH, NH₂ | (CH₃)₂N-C₆H₄-[squarate-NH-*CH(CH₃)CH₂OH] |
| 9 | (CH₃)₂N-C₆H₄-[squarate-Cl] | CH₃*CHCO₂CH₃·HCl, NH₂ | (CH₃)₂N-C₆H₄-[squarate-NH-*CH(CH₃)CO₂CH₃] |
| 10 | (CH₃)₂N-C₆H₄-[squarate-Cl] | C₆H₅CH₂*CHCH₂OH, NH₂ | (CH₃)₂N-C₆H₄-[squarate-NH-*CH(CH₂C₆H₅)CH₂OH] |
| 11 | (CH₃)₂N-C₆H₄-[squarate-Cl] | C₂H₅*CHCH₂OH, NH₂ | (CH₃)₂N-C₆H₄-[squarate-NH-*CH(C₂H₅)CH₂OH] |
| 12 | (CH₃)₂N-C₆H₄-[squarate-Cl] | (CH₃)₂CH*CHCO₂CH₃, NH₂ | (CH₃)₂N-C₆H₄-[squarate-NH-*CH(CH(CH₃)₂)CO₂CH₃] |
| 13 | (CH₃)₂N-C₆H₄-[squarate-Cl] | CH₃CH(OH)*CHCO₂CH₃, NH₂ | (CH₃)₂N-C₆H₄-[squarate-NH-*CH(CH(OH)CH₃)CO₂CH₃] |

TABLE 3-continued

| Example No. | Formula II (Squarylium Derivative) | Formula (IIIb) (Amino Compound) | Formula (I) (Objective Product) |
|---|---|---|---|
| 14 | (CH₃)₂N-C₆H₄-[squarylium-Cl, =O, =O] | CH₃CH*—CO₂CH₂C₆H₅, NH₂ | (CH₃)₂N-C₆H₄-[squarylium-NH-CH*(CH₃)CO₂CH₂C₆H₅, =O, =O] |
| 15 | (CH₃)₂N-C₆H₄-[squarylium-Cl, =O, =O] | CH₃CH*CO₂-t-C₄H₉, NH₂ | (CH₃)₂N-C₆H₄-[squarylium-NH-CH*(CH₃)CO₂-t-C₄H₉, =O, =O] |
| 16 | (CH₃)₂N-C₆H₄-[squarylium-Cl, =O, =O] | C₆H₅CH₂CH*CO₂CH₃, NH₂ | (CH₃)₂N-C₆H₄-[squarylium-NH-CH*(CH₂C₆H₅)CO₂CH₃, =O, =O] |
| 17 | (CH₃)₂N-C₆H₄-[squarylium-Cl, =O, =O] | (CH₃)₂CHCH₂CH*CO₂CH₃, NH₂ | (CH₃)₂N-C₆H₄-[squarylium-NH-CH*(CH₂CH(CH₃)₂)CO₂CH₃, =O, =O] |
| 18 | (CH₃)₂N-C₆H₄-[squarylium-Cl, =O, =O] | C₂H₅-CH(CH₃)-CH*CO₂CH₃, NH₂ | (CH₃)₂N-C₆H₄-[squarylium-NH-CH*(CH(CH₃)C₂H₅)CO₂CH₃, =O, =O] |
| 19 | (CH₃)₂N-C₆H₄-[squarylium-Cl, =O, =O] | (CH₃)₂CHCH₂CH*CO₂-t-C₄H₉, NH₂ | (CH₃)₂N-C₆H₄-[squarylium-NH-CH*(CH₂CH(CH₃)₂)CO₂-t-C₄H₉, =O, =O] |

TABLE 3-continued

| Example No. | Formula II (Squarylium Derivative) | Formula (IIIb) (Amino Compound) | Formula (I) (Objective Product) |
|---|---|---|---|
| 20 | (CH₃)₂N-C₆H₃(CH₃)- squaryl-Cl | C₆H₅CH₂*CHCO₂-t-C₄H₉ \| NH₂ | C₆H₅CH₂*CHCO₂-t-C₄H₉ \| NH-squaryl-C₆H₄-N(CH₃)₂ |
| 21 | (CH₃)₂N-C₆H₄- squaryl-Cl | CH₃O₂CCH₂*CHCO₂CH₃ \| NH₂ | CH₃O₂CCH₂*CHCO₂CH₃ \| NH-squaryl-C₆H₄-N(CH₃)₂ |
| 22 | (CH₃)₂N-C₆H₃(CH₃)- squaryl-Cl | CH₃*CHCH₂OH \| NH₂ | CH₃*CHCH₂OH \| NH-squaryl |
| 23 | (CH₃)₂N-C₆H₃(CH₃)- squaryl-Cl | OH \| C₂H₅CHCH₂NH₂* | OH \| NHCH₂*CHC₂H₅ |
| 24 | (CH₃)₂N-C₆H₃(CH₃)- squaryl-Cl | OH \| CH₃CHCH₂NH₂* | OH \| NHCH₂*CHCH₃ |
| 25 | (CH₃)₂N-C₆H₃(CH₃)- squaryl-Cl | C₂H₅*CHCH₂OH \| NH₂ | C₂H₅*CHCH₂OH \| NH-squaryl |
| 26 | (CH₃)₂N-C₆H₃(CH₃)- squaryl-Cl | CH₃*CHCO₂CH₃ \| NH₂ | CH₃*CHCO₂CH₃ \| NH-squaryl |

TABLE 3-continued

| Example No. | Formula II (Squarylium Derivative) | Formula (IIIb) (Amino Compound) | Formula (I) (Objective Product) |
| --- | --- | --- | --- |
| 27 | 4-(dimethylamino)-2-methylphenyl chloro squarate | (CH₃)₂CHCH₂*CH(NH₂)CO₂-t-C₄H₉ | corresponding squarylium amide |
| 28 | 4-(dimethylamino)-2-methylphenyl chloro squarate | C₂H₅(CH₃)*CHCHCO₂CH₃ with NH₂ | corresponding squarylium amide |
| 29 | 4-(dimethylamino)-2-ethylphenyl chloro squarate | CH₃CH(OH)CH₂NH₂ (* on CH) | corresponding squarylium amide |
| 30 | 4-(dimethylamino)-2-ethylphenyl chloro squarate | *CH₃CH(NH₂)CH₂OH | corresponding squarylium amide |
| 31 | 4-(dimethylamino)-2-ethylphenyl chloro squarate | C₂H₅CH(OH)CH₂NH₂ (* on CH) | corresponding squarylium amide |
| 32 | 4-(dimethylamino)-2-ethylphenyl chloro squarate | *C₂H₅CH(NH₂)CH₂OH | corresponding squarylium amide |

TABLE 3-continued

| Example No. | Formula II (Squarylium Derivative) | Formula (IIIb) (Amino Compound) | Formula (I) (Objective Product) |
|---|---|---|---|
| 33 | [structure] | C₆H₅CH₂*CHCH₂OH / NH₂ | [structure] |
| 34 | [structure] | OH / CH₃*CHCH₂NH₂ | [structure] |
| 35 | [structure] | CH₃*CHCH₂OH / NH₂ | [structure] |
| 36 | [structure] | OH / C₂H₅*CHCH₂NH₂ | [structure] |
| 37 | [structure] | C₂H₅*CHCH₂OH / NH₂ | [structure] |

TABLE 4

| Example No. | Elementary Analysis (Calcd./Found) | | | $\lambda_{max}$ (nm) (solvent) | Melting Point (°C.) |
|---|---|---|---|---|---|
| | C | H | N | | |
| 8 | 65.67/65.91 | 6.61/6.50 | 10.21/10.10 | 396 (C₂H₅OH) | 219 |
| 9 | 63.56/63.32 | 6.00/5.82 | 9.27/9.35 | 410 (CH₂Cl₂) | 217 |
| 10 | 71.98/71.62 | 6.33/6.31 | 8.06/7.82 | 401 (CH₂Cl₂) | 192 |
| 11 | 66.64/66.24 | 6.99/6.86 | 9.72/9.81 | 396 (C₂H₅OH) | 201 |
| 12 | 65.43/65.91 | 6.71/6.50 | 8.84/8.72 | 402 (CHCl₃) | 153 |
| 13 | 67.98/68.74 | 6.71/6.70 | 9.33/9.31 | 402 (CH₂Cl₂) | 176 |
| 14 | 69.82/69.50 | 5.86/5.56 | 7.40/7.25 | 402 (CHCl₃) | 181 |
| 15 | 66.26/66.70 | 7.02/7.12 | 8.14/8.02 | 402 (CHCl₃) | 174 |
| 16 | 69.82/69.50 | 5.86/5.84 | 7.40/7.52 | 402 (CH₂Cl₂) | 207 |
| 17 | 66.26/66.04 | 7.02/7.12 | 8.14/8.25 | 402 (CH₂Cl₂) | 185 |
| 18 | 66.26/66.52 | 7.02/7.10 | 8.14/8.02 | 402 (CHCl₃) | 158 |
| 19 | 68.37/68.17 | 7.82/7.80 | 7.25/7.20 | 402 (CHCl₃) | 177 |
| 20 | 71.40/71.15 | 6.71/6.62 | 6.66/6.60 | 403 (CHCl₃) | 159 |
| 21 | 59.99/59.82 | 5.59/5.63 | 7.78/7.88 | 404 (CHCl₃) | 186 |
| 22 | 66.43/66.21 | 6.99/6.09 | 9.72/9.70 | 403 (CH₂Cl₂) | 160 |
| 23 | 67.52/67.21 | 7.33/7.21 | 9.27/9.15 | 403 (CH₂Cl₂) | 143 |

TABLE 4-continued

| Example No. | Elementary Analysis (Calcd./Found) C | H | N | $\lambda_{max}$ (nm) (solvent) | Melting Point (°C.) |
|---|---|---|---|---|---|
| 24 | 66.64/66.38 | 6.99/6.82 | 9.72/9.50 | 403 (CH$_2$Cl$_2$) | 161 |
| 25 | 67.52/67.61 | 7.33/7.20 | 9.27/9.05 | 402 (CH$_2$Cl$_2$) | 166 |
| 26 | 64.54/64.82 | 6.37/6.32 | 8.86/8.88 | 404 (CH$_2$Cl$_2$) | 142 |
| 27 | 68.97/68.95 | 8.05/8.03 | 7.00/7.05 | 403 (CH$_2$Cl$_2$) | 148 |
| 28 | 67.01/66.92 | 7.31/7.33 | 7.82/7.80 | 404 (CH$_2$Cl$_2$) | 116 |
| 29 | 67.52/67.50 | 7.34/7.14 | 9.27/9.25 | 402 (CH$_2$Cl$_2$) | 140 |
| 30 | 67.52/67.48 | 7.34/7.21 | 9.27/9.07 | 402 (CH$_2$Cl$_2$) | 147 |
| 31 | 68.33/68.21 | 7.65/7.63 | 8.86/8.91 | 402 (CH$_2$Cl$_2$) | 120 |
| 32 | 68.33/68.42 | 7.65/7.61 | 8.86/8.92 | 402 (CH$_2$Cl$_2$) | 176 |
| 33 | 69.45/69.83 | 6.36/6.46 | 7.37/7.25 | 411 (CH$_2$Cl$_2$) | 128 |
| 34 | 63.14/63.25 | 6.62/6.30 | 9.21/9.32 | 410 (CH$_2$Cl$_2$) | 216 |
| 35 | 63.14/64.01 | 6.62/6.60 | 9.21/9.40 | 411 (CH$_2$Cl$_2$) | 188 |
| 36 | 64.13/64.62 | 6.97/6.82 | 8.80/8.62 | 410 (CH$_2$Cl$_2$) | 106 |
| 37 | 64.13/64.01 | 6.97/6.95 | 8.80/8.78 | 410 (CH$_2$Cl$_2$) | 153 |

REFERENCE EXAMPLE 1

A glass cell was filled with a powder of the compound represented by the above structural formula (I') which was described in Example 1, and the Nd:YAG laser (wavelength: 1.064 m, output: 180 mJ/pulse) was irradiated thereto. As a result, scattered green light of 532 nm due to SHG was generated. Its strength measured was 8 times that of powdered urea measured under the same conditions as above.

REFERENCE EXAMPLE 2

A glass cell was filled with a powder of the compound represented by the above structural formula (I-1) which was described in Example 5, and the Nd:YAG laser (wavelength: 1.064 m, output: 180 mJ/pulse) was irradiated thereto. As a result, scattered green light of 532 nm due to SHG was generated. Its strength measured was about 70 times that of powdered urea measured under the same conditions as above.

The squarylium derivative of the present invention represented by the above general formula (I) is a novel compound and shows high nonlinearity. This derivative is also a substance excellent in thermal resistance, light resistance, storage stability and processability. It can be therefore used for preparation of nonlinear optical elements such as optical wavelength conversion elements, optical shutters, high speed switching elements, optical logical circuits and optical transistors.

While the invention has been described in detail and with reference to specific embodiments thereof, it will be apparent to one skilled in the art that various changes and modifications can be made therein without depending from the spirit and scope thereof.

What is claimed is:

1. A squarylium derivative represented by the following general formula (I):

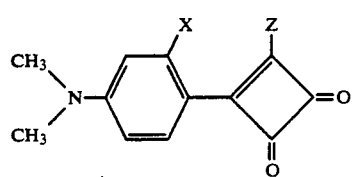

wherein X represents a hydrogen atom, a methyl group, an ethyl group or a methoxy group; and Z represents

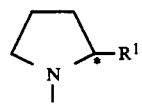

or —NHR$^2$ wherein R$^1$ represents —CO$_2$—t—C$_4$H$_9$ or —CH$_2$OH and R$^2$ represents —CH$_2$CH$_2$OH,

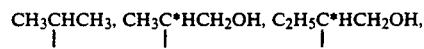

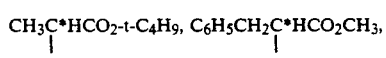

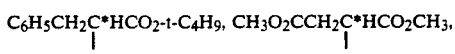

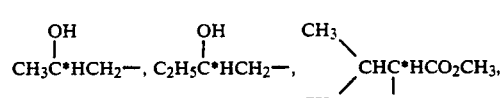

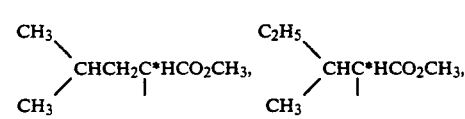

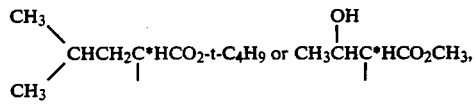

wherein C* means an asymmetric carbon atom.

2. A squarylium derivative as in claim 1, wherein said Z is a group represented by

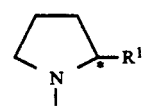

3. A squarylium derivative as in claim 1, wherein said Z is a group represented by —NHR$^2$.

* * * * *